(12) United States Patent
Trobaugh et al.

(10) Patent No.: US 9,498,134 B1
(45) Date of Patent: Nov. 22, 2016

(54) DIFFUSE OPTICAL TOMOGRAPHY METHODS AND SYSTEM FOR DETERMINING OPTICAL PROPERTIES

(71) Applicant: Cephalogics, LLC, Boston, MA (US)

(72) Inventors: Jason W. Trobaugh, St. Louis, MO (US); Chandran V. Seshagiri, Arlington, MA (US); Bertan Hallacoglu, Boston, MA (US)

(73) Assignee: Cephalogics, LLC, Boston, MA (US)

( * ) Notice: Subject to any disclaimer, the term of this patent is extended or adjusted under 35 U.S.C. 154(b) by 0 days.

(21) Appl. No.: 15/083,010

(22) Filed: Mar. 28, 2016

(51) Int. Cl.
*A61B 5/00* (2006.01)
*A61B 5/1455* (2006.01)
*A61B 5/145* (2006.01)

(52) U.S. Cl.
CPC ......... *A61B 5/0042* (2013.01); *A61B 5/14546* (2013.01); *A61B 5/14553* (2013.01); *A61B 5/742* (2013.01); *A61B 2562/0238* (2013.01); *A61B 2562/164* (2013.01); *A61B 2576/026* (2013.01)

(58) Field of Classification Search
None
See application file for complete search history.

(56) References Cited

U.S. PATENT DOCUMENTS

| | | | |
|---|---|---|---|
| 5,584,296 A | 12/1996 | Cui et al. | |
| 7,072,701 B2 | 7/2006 | Chen et al. | |
| 7,983,740 B2 | 7/2011 | Culver et al. | |
| 8,509,866 B2 | 8/2013 | Schmitt et al. | |
| 2008/0154126 A1 | 6/2008 | Culver et al. | |
| 2009/0292210 A1 | 11/2009 | Culver et al. | |
| 2010/0016732 A1* | 1/2010 | Wells | A61B 5/0059 600/476 |
| 2010/0234706 A1 | 9/2010 | Gilland | |
| 2010/0241006 A1 | 9/2010 | Choi et al. | |
| 2011/0112379 A1 | 5/2011 | Li et al. | |
| 2014/0275891 A1* | 9/2014 | Muehlemann | A61B 5/0013 600/328 |
| 2014/0276013 A1 | 9/2014 | Muehlemann et al. | |
| 2014/0276014 A1* | 9/2014 | Khanicheh | A61B 5/0013 600/425 |

OTHER PUBLICATIONS

Boas, A fundamental limitation of linearized algorithms for diffuse optical tomography. Opt Express. Dec. 22, 1997;1(13):404-13.
Culver et al., Diffuse Optical Tomography of Cerebral Blood Flow, Oxygenation, and Metabolism in Rat During Focal Ischemia. J Cereb Blood Flow Metab. 2003;23(8):911-24.
Dehghani et al., Application of Spectral Derivative data in spectral Near Infrared Tomography. Proc SPIE. Feb. 2011;7896:78960I.1-7. doi: 10.1117/12.873940.
Dehghani et al., Application of spectral derivative data in visible and nearinfrared spectroscopy. Phys Med Biol. Jun 21, 2010; 55(12):3381-99. doi:10.1088/0031-9155/55/12/008. Epub Jun. 21, 2011. 26 pages.
Dehghani et al., Near infrared optical tomography using NIRFAST: Algorithm for numerical model and image reconstruction. Comm Numer Meth Eng. Jun. 25, 2008. doi: 10.1002/cnm.1162. 22 pages.

(Continued)

*Primary Examiner* — Tse Chen
*Assistant Examiner* — Joanne Hoffman
(74) *Attorney, Agent, or Firm* — Wolf, Greenfield & Sacks, P.C.

(57) ABSTRACT

Optical source and detector arrangements, systems, and methods are described, which may be used to provide or analyze information about a subject, including hemoglobin and deoxygenated hemoglobin concentrations. Multiple optical detectors can be positioned at different distances from an optical source. The optical sources may irradiate the subject with optical signals and the optical detectors can detect the optical signals from the optical sources after passing through the subject. Analysis of the detected signals source can yield information about the subject.

11 Claims, 6 Drawing Sheets

(56) References Cited

OTHER PUBLICATIONS

Dehghani et al., Numerical modelling and image reconstruction in diffuse optical tomography. Phil Trans R Soc A. Jul. 6, 2009;367:3073-93.

Diiulio, Interview with an Inventor: Joseph P Culver, PhD, discusses diffuse optical tomography with Medical Imaging. MRI & CT. Jun. 2007;10. medicalimagingmag.com.

Durduran et al., Diffuse optics for tissue monitoring and tomography. Rep Prog Phys. Jun. 2, 2010;73:076701. 43 pages.

Ferradal et al., Bedside Monitoring of Cerebral Oxygenation Using DOT. Biomed Optics. BIOMED/DH Joint Poster Session. Apr. 11-14, 2010. 3 pages.

Liao et al., Neonatal hemodynamic response to visual cortex activity: high-density near-infrared spectroscopy study. J Biomed Optics. Mar./Apr. 2010;15(2):026010.1-9.

Nellcor, A Technology Overview of the Nellcor™ OxiMax Pulse Oximetry System. White Paper. 11-PM-0270 MN17702.2011. 8 pages.

O'Leary, Imaging with Diffuse Photon Density Waves. Thesis. University of Pennsylvania, Department of Physics. 1996. 206 pages.

White et al., Phase-encoded retinotopy as an evaluation of diffuse optical neuroimaging. NeuroImage. 2010;49:568-77.

White et al., Quantitative evaluation of high-density diffuse optical tomography: in vivo resolution and mapping performance. J Biomed Optics. Mar./Apr. 2010;15(2):026006.1-14.

White et al., Resting-state functional connectivity in the human brain revealed with diffuse optical tomography. NeuroImage. 2009;47:148-56.

Zeff et al., Retinotopic mapping of adult human visual cortex with high-density diffuse optical tomography. PNAS. Jul. 17, 2007;104(29):12169-74.

\* cited by examiner

DIFFUSE OPTICAL TOMOGRAPHY METHODS AND SYSTEM FOR DETERMINING OPTICAL PROPERTIES

BACKGROUND

Field

The present application relates to optical tomography systems and sensors and related apparatus and methods.

Related Art

Diagnostic instruments for monitoring properties of the brain include magnetic resonance imaging (MRI) devices, computed tomography (CT) devices, microdialysis devices, intracranial pressure monitors, cerebral oximeters, transcranial Doppler devices, oxygen catheters, x-ray devices, electroencephalography devices, positron emission tomography devices, single-photon emission computed tomography (SPECT) devices, magnetoencephalography devices, ultrasound devices, and optically-based instrumentation. Some such instruments are placed in proximity to the patient's head. Optically-based sensors for analyzing medical patients are known and optical tomography is a known technique for optically inspecting a specimen.

BRIEF SUMMARY

According to an aspect of the present application an apparatus is provided. The apparatus comprises a first optical source disposed at a first position and configured to emit a first optical signal of a first wavelength and an arrangement of optical detectors, at least some of which are positioned at different distances from the first optical source. The arrangement of optical detectors include a first subset of optical detectors positioned a first distance from the first optical source and a second subset of optical detectors positioned a second distance from the first optical source. The first subset of optical detectors and the second subset of optical detectors are configured to receive the first optical signal. A first optical detector of the first subset of optical detectors is configured to produce at least one first output signal indicative of a first received optical intensity of the first optical signal. A second optical detector of the second subset of optical detectors is configured to produce at least one second output signal indicative of a second received optical intensity of the first optical signal. A distance between the first optical detector and the second optical detector is a smallest distance from among a plurality of distances between optical detectors of the second subset and the first optical detector. The apparatus further comprises a processor coupled to the first and second optical detectors and configured to receive the at least one first output signal from the first optical detector and the at least one second output signal from the second optical detector. The processor is further configured to process in combination the at least one first output signal and the at least one second output signal.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Aspects of the present application provided diffuse optical tomography (DOT) apparatus and methods for determining absolute values of a property in a region of a subject. The property may include a biological property of interest, such as oxygenated hemoglobin (HbO) and de-oxygenated hemoglobin (HbR) levels, total hemoglobin levels (tHb), or other metrics of interest. By performing diffuse optical tomography on the subject's head in accordance with aspects of the present application, absolute values of one or more properties of the subject's brain, such as HbO and HbR levels, may be obtained and provide information that facilitates analysis of the subject's brain and/or condition.

According to one aspect, a DOT device includes multiple optical sources and multiple optical detectors arranged such that, for a given optical source there are multiple optical detectors which detect an optical signal emitted by the optical source, at least two of which are positioned at different distances from the optical source. Positioning the DOT device on a subject's head may allow optical signals emitted by the optical source to pass through a portion of the subject's head to the two optical detectors located at different distances. The intensity of an optical signal detected by an optical detector may depend on the optical path length of the optical signal from the optical source to that optical detector. The resulting differences in intensity of the optical signals received by the two optical detectors located at different distances from the optical source may be used to determine absolute values for one or more properties of the subject's head, such as HbO and HbR in some embodiments. The absolute values may correspond to different regions of the subject because the optical signals traveled different paths between the optical source and the two (or more) optical detectors located at different distances. In some embodiments, the resulting absolute values of biological and/or optical properties may be used to generate an image of the subject by mapping the absolute values to regions in the image that correspond to locations within the subject. In some embodiments, intensity of optical signals received by the optical detectors may provide relative values for one or more properties of the subject's head, which may be used to generate an image of the subject, including a target tissue (e.g., brain) of the subject. The relative values can refer to differences in a property at different locations within the subject's head. Such relative values may contrast with a differential value acquired by measuring a temporal change in a property for a region of the subject. For example, a relative value for one location of the subject's head may indicate whether the property has a high or low value in comparison to another location of the subject's head.

According to an aspect of the present application, there may be for an array, or more generally an arrangement, of optical sources and detectors, multiple combinations of measured intensities detected by at least two optical detectors detecting an optical signal emitted by an optical source. Certain combinations of such measurements may yield valuable information about the optical and/or biological properties of a subject. The array of optical detectors and optical sources may provide (at least partial) redundancy in optical signals passing through the same region of the subject. The detected optical signals from two or more optical detectors may be used to determine an optical property for a region of the subject where the optical path lengths overlap. In this manner, optical properties for discretized volumes within the subject may be determined from measurements provided by various combinations of optical detectors and optical sources emitting the optical signals detected by the optical detectors. Accordingly, an aspect of the present application provides techniques for selecting appropriate combinations of optical detectors and optical sources to provide valuable information about a subject, such as the absolute values of optical and/or biological properties for discrete regions of a subject with a desired level of precision. The manner in which optical intensities measured by optical detectors at different distances from an optical source are combined may occur through a variety of suitable techniques including a ratio of values corresponding to optical intensities and/or a difference of values corresponding to optical intensities. In some embodiments, a comparison in measured optical intensities detected by optical detectors at different locations of the subject may be determined, whether by subtraction, taking a ratio, or otherwise, and may be referred to herein as a "spatial differential." Such techniques may reduce noise in the results by accounting for variability in output power of optical sources in the array. When a sensor is positioned to measure optical properties of a subject, variation in the amount of light that couples from individual optical sources to the subject may occur. The spatial differential technique may also reduce artifacts that arise from such variation in optical coupling. The spatial differential may have a logarithmic form such that the comparison of the measured optical intensities can be determined by calculating the logarithm of a ratio of optical intensities, which can also be determined by calculating a difference between values corresponding to the optical intensities. In some embodiments, the spatial differential may be determined by comparing measured optical intensities detected by optical detectors at different distances from the same optical source.

The biological properties of a subject, such as chromophore concentrations, may impact the optical properties of the subject. Certain quantities of interest in the subject, such as oxygen saturation, may be determined by assessing the optical properties of the subject to provide an estimated value for a quantity of interest. The biological tissue of a subject may have chromophores (e.g., hemoglobin) which may interact with light such that intensity detected by the optical detectors depends on the concentration and/or type of chromophores present in the biological tissue. For example, in biological tissue, absorption of light at wavelengths in the 600 to 900 nm range depends primarily on hemoglobin, lipids, melanin and water. Absorption due to oxygenated and deoxygenated hemoglobin varies with the wavelength throughout this range in consistent and predictable ways. Thus, light absorption measurements at two or more wavelengths within this range may be used to estimate concentrations of oxygenated and de-oxygenated hemoglobin. In a particular tissue, absorption may be estimated from detecting light intensity at two or more distances from a light source. From estimates of the optical absorption at two or more wavelengths, concentrations of oxygenated and de-oxygenated hemoglobin may be estimated. Total hemoglobin concentration may be calculated as a sum of the oxygenated and deoxygenated hemoglobin concentrations. In some embodiments, total hemoglobin concentration may be calculated by the absorption of particular tissue at a single wavelength (e.g., 808 nm) where the contributions from oxygenated hemoglobin and deoxygenated hemoglobin to the optical signal are equal.

An aspect of the application provides an optical source of the DOT device configured to emit multiple wavelengths. An optical source may emit optical signals at two or more wavelengths. The intensity of the optical signals detected by optical detectors of the DOT device may be used to estimate absorption properties of a region of a subject through which the optical signals passed. Using an optical source configured to emit optical signals at different wavelengths may allow for determination of absolute value concentration estimates or relative value concentration estimates through suitable processing of the detected optical signals, rather than a change in concentration between measurements over time as in conventional DOT measurements. Such techniques may allow for determination of absolute values for concentrations of oxygenated hemoglobin (HbO), de-oxygenated hemoglobin (HbR), and/or oxygen saturation ($StO_2$).

Other optical properties of the region of interest in a subject besides absorption, such as scattering, may vary across subjects and contribute to the intensity of the optical signals detected by the optical detectors. The variation in scattering that arises from differences in geometry and material in regions of interest (e.g., a subject's head) across subjects may contribute to the intensity difference between optical signals at different wavelengths, which may bias the estimated absorption and/or the estimated concentration value. The amount of scattering bias may vary across subjects, which can be challenging to overcome through the use of models or other computational techniques. The accuracy of absolute values of biological properties that depend on the absorption properties of a region of a subject may be improved by accounting for this variation in scattering by using techniques that improve the consistency in which scattering biases the results. Accordingly, some aspects of the application include an optical source configured to emit a wavelength as a reference wavelength for the other wavelengths emitted by the optical source. Data from the detected intensity of the reference wavelength may provide one or more benefits. Data from the detected intensity of the reference wavelength may reduce bias arising from scattering mismatch of an absorption value and/or a concentration value determined from different wavelengths. In this manner, the reference wavelength may effectively normalize contributions due to scattering in the determination of absorption values and/or concentration values for a tissue. A combination of the detected intensity corresponding to the reference wavelength and another wavelength may improve the accuracy of the absolute value for a property in a region of a subject. The combination may include a difference and/or a ratio between the detected intensity of the reference wavelength and the other wavelength.

Data associated with the reference wavelength may also be used to reduce noise artifacts that are substantially common across different wavelengths, such as noise artifacts that are independent of the wavelength. One type of noise arises from variation in optical coupling of light with different regions of the subject. Combining the detected intensity corresponding to the reference wavelength and another wavelength may account for such optical coupling variation because the amount of optical coupling at a location of the subject may be similar for both the reference wavelength and the other wavelength.

According to an aspect of the application, a matrix of values (referred herein as an "A-matrix") may be used to relate optical properties of the region to intensity detected by optical detectors of the DOT device. The region may be divided into voxels such that an absolute value for an optical property is determined for each voxel. An optical signal may pass through multiple voxels such that the detected intensity reflects the optical properties of the multiple voxels. Accordingly, values within the A-matrix may indicate how properties within individual voxels of the region affect the detected intensity. The A-matrix may provide a linear relationship between a difference in optical intensity for a corresponding change in optical absorption. In some embodiments, this relationship may be a temporal relationship for a particular optical detector. In some embodiments, this relationship may be a spatial relationship between different detectors. In this manner, absolute values of optical properties for different voxels may be determined based on the A-matrix and the detected intensity from different optical detectors. In some embodiments, an A-matrix may be constructed to account for determining absolute values of optical properties based on, for example, a difference or ratio of intensity detected at two optical detectors having different distances from optical signals emitted by an optical source. Values in the A-matrix may depend on distances between optical sources and optical detectors. Accordingly, aspects of the application provide techniques for determining an A-matrix to account for changes in distances between optical sources and detectors as the DOT device conforms to a subject.

The aspects and embodiments described above, as well as additional aspects and embodiments, are described further below. These aspects and/or embodiments may be used individually, all together, or in any combination of two or more, as the application is not limited in this respect.

Figure 1:
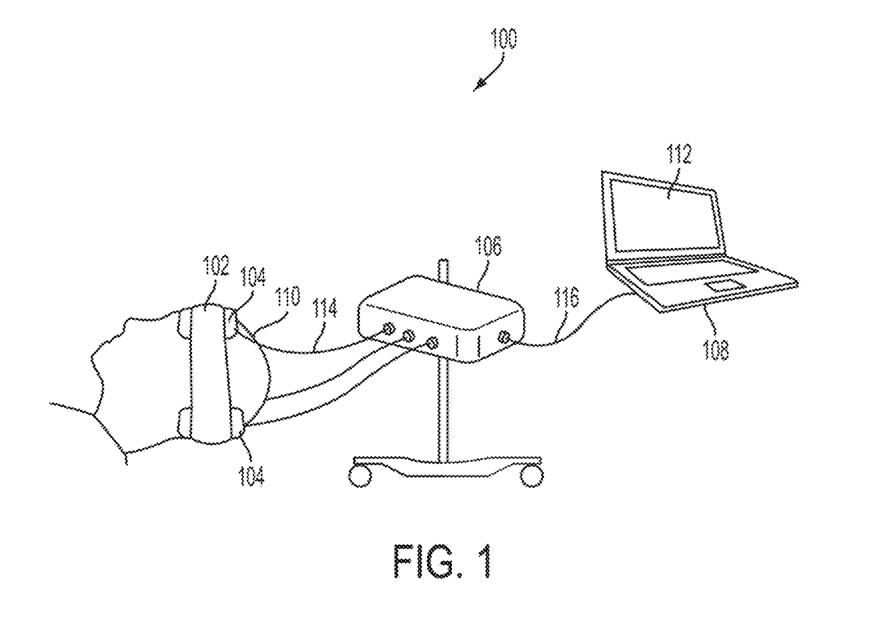
FIG. 1 illustrates a system for performing optical tomography measurements on a subject's head, according to a non-limiting embodiment.

A non-limiting example of a system for performing DOT analysis of a subject's head is shown in FIG. 1. System 100 includes a support 102, one or more sensors 104 (two of which are shown), a host module 106 (which may also be referred to herein simply as a "host"), and a central unit 108 (which may also be referred to herein as a "master"). The support 102 may support a sensor 104 in relation to the head 110 of a subject (e.g., a medical patient). Thus, the support 102 may represent a headpiece in some embodiments. The system may irradiate the subject's head with optical emissions from the sensor 104 and detect and process optical emissions received from the head, including the original optical emissions emitted by the sensor 104 and/or optical emissions triggered inside the subject in response to original optical emissions from the sensor 104. The host module 106 and central unit 108 may perform various functions, including controlling operation of the sensor 104 and processing the collected data. For example, each of the host module 106 and central unit 108 may include one or more processors, and may perform the various signal processing described further below.

The system 100 may be used to provide and/or determine information relating to various physical properties and/or conditions of the subject. The intensity, phase, and/or frequency of optical signals detected by an optical detector may be used to provide information relating to one or more properties of the subject, which may be used to assess a condition of the subject. In some embodiments, however, the phase need not be considered in the determination of any biological properties of interest. The system 100 may be used to provide information relating to absorption of endogenous biological chromophores, such as oxygenated hemoglobin, deoxygenated hemoglobin, lipids, water, myoglobin, bilirubin, and/or cytochrome C oxidase. Measured absorption properties may allow for determination of oxygenated and deoxygenated hemoglobin concentration and tissue oxygen saturation ($HbO_2$/tHb).

The system 100 may be configured to measure absolute values of optical properties spatially based on the positioning of the sensors and any constituent optical sources and detectors relative to the subject. One or more images may be generated from the resulting data. In some embodiments, multiple areas or regions of a subject may be imaged substantially simultaneously and allow comparison of image results for the different areas or regions.

The support 102, sensor 104, host module 106, and central unit 108 of system 100 may take various forms. The sensor 104 may include suitable components for generating and/or receiving optical signals for performing DOT measurements (using near infrared spectroscopy (NIRS) techniques, for example), including one or more optical sources and/or one or more optical detectors. As shown, the sensor 104 may be configured to optically couple to a subject's head (or other region of interest of a subject), for instance on an external surface of the subject's head (e.g., the scalp) without any need to remove or modify portions of the subject's skull and/or scalp. In some embodiments, the sensor 104 may be flexible to conform to the subject's head. The support 102 may hold or otherwise support the sensor 104 against the subject's head, and may have any suitable construction for doing so.

The host module 106 may be coupled to the sensor 104 by a cabled or wireless connector 114 and may perform various functions with respect to the sensor 104, including controlling operation of the sensor 104 to at least some extent. For example, the host module may communicate control signals to the sensor 104 to control activation of the sensor 104 and/or may receive signals from the sensor 104 representative of the optical signals detected by the sensor 104. The host module 106 may also serve as a communication relay between the sensor 104 and the central unit 108, for example in some embodiments integrating or grouping data (e.g., data packets) from multiple optical detectors into a frame prior to sending to the central unit 108. The host module may be implemented in any suitable form.

The central unit 108, which may be implemented in any suitable form, may be coupled to the host module by a cabled or wireless connection 116 and may perform various control functionality for the system. For example, the central unit 108 may include a user interface via which a user (e.g., a doctor, clinician, or other user) may select the conditions of a test or monitoring event to be performed on the subject. The central unit 108 may provide to the host module 106 suitable control signals relating to the selected test or monitoring event. The host module 106 may, in turn, provide suitable control signals to the sensor 104 to cause production and collection of optical emissions. Collected signals may then be provided to the central unit 108 via the host module 106, and the central unit may, for example, perform post processing of the signals. In some embodiments, the central unit 108 may control display of collected information, for example in textual and/or graphical form on a display 112. An example of an image which may be generated according to aspects of the present application is described below in connection with FIG. 6. In some embodiments, the central unit may control analysis and/or display of images and/or information relating to two or more regions (or portions) of a subject's brain simultaneously (e.g., two hemispheres of the subject's brain). For example, referring to FIG. 3A, an image of both hemispheres 308a and 308b of a subject's brain may be produced from information collected by the three illustrated optical sensors, and such images may be displayed to a user, for example to allow for analysis of a condition or characteristic of the subject.

While the system 100 of FIG. 1 is shown as including a distinct host module 106 and central unit 108, it should be appreciated that not all embodiments are limited in this respect. For example, in some embodiments, the host module 106 and the central unit 108 may be integrated as a single unit.

An optical system for using DOT to analyze a subject, such as system 100 of FIG. 1, may use any suitable sensor 104. An optical array may include a plurality of optical sources and a plurality of optical detectors. The optical sources and optical detectors may be formed on or otherwise connected by a common substrate, which may be flexible in some embodiments, allowing the optical sensor to be placed in contact with, and to conform to, a subject of interest or portion thereof (e.g., a subject's head). Optical sources and optical detectors in the sensor may have any suitable size, shape, and arrangement within the array to perform DOT measurements.

Figure 2A:
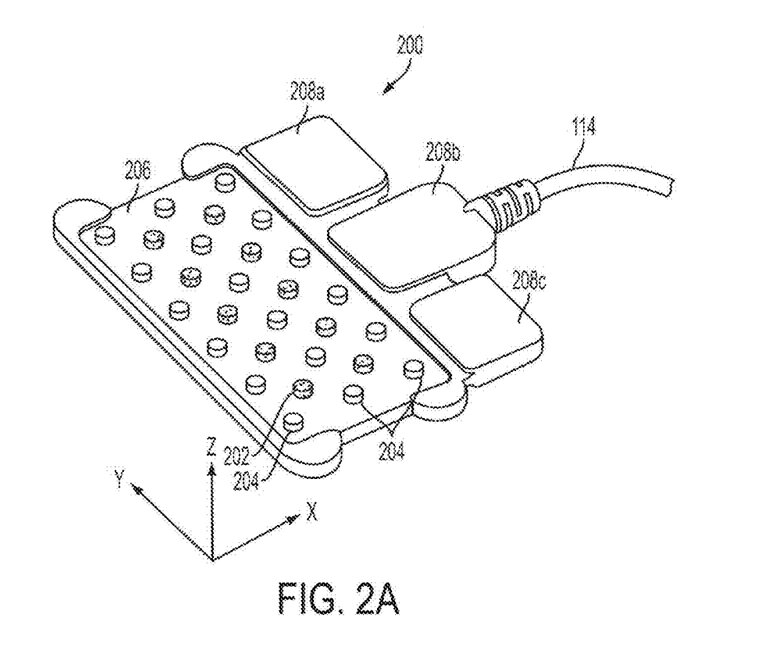
FIGS. 2A and 2B illustrate a top view and a bottom view, respectively, of an optical sensor which may be used in the system of FIG. 1, according to a non-limiting embodiment.
Figure 2B:
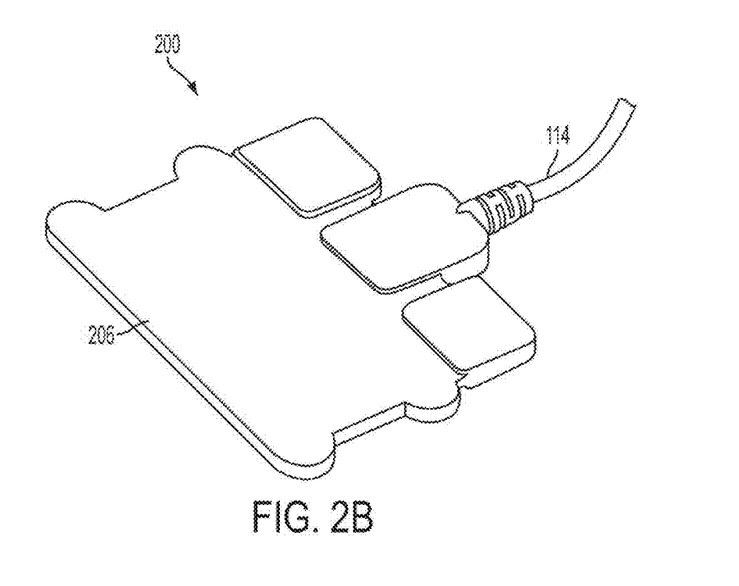

A non-limiting example is illustrated in FIGS. 2A and 2B, which show a top view and bottom view, respectively, of an optical sensor 200 which may be used in the system of FIG. 1, for example as sensor 104, according to a non-limiting embodiment. The sensor 200 includes a plurality of optical sources 202 (shown with dotted fill), totaling ten in all, and a plurality of optical detectors 204, totaling eighteen in all, and which in the non-limiting example illustrated are at least partially encapsulated in a support structure 206. In the non-limiting example of FIG. 2A, the optical sources 202 and optical detectors 204 are arranged in alternating rows that are offset from each other. The optical sensor 200 may further include circuitry 208a, 208b, and 208c, such as analog and/or digital circuitry for controlling operation of and processing of signals from the optical sources 202 and/or optical detectors 204. Optical sensor 200 may be configured to be placed in contact with (or at least in close proximity to) a subject (e.g., a patient), for example on an exterior surface of the subject, such that the optical sources 202 irradiate the subject with optical signals (e.g., near infrared (NIR) signals) and optical detectors 204 receive the optical signals from the subject, which in some embodiments occurs after they pass through the subject.

Figure 3A:
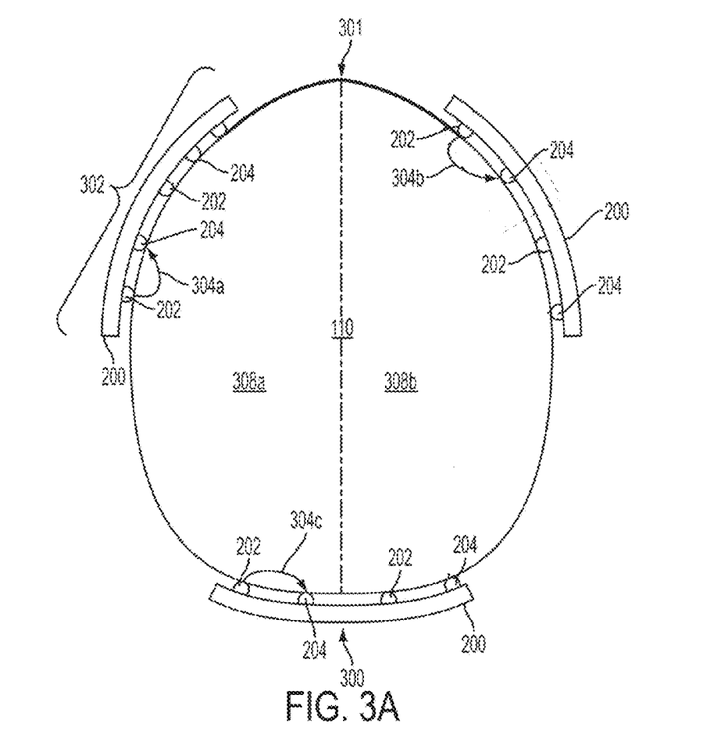
FIG. 3A illustrates a top view of a subject's head against which three optical sensors according to an aspect of the present application are placed.

FIG. 3A illustrates a top view of a subject's head 110 against which three optical sensors 200 are placed. One of the optical sensors 200 is placed centrally on the back 300 of the head 110 while the other two optical sensors 200 are placed bilaterally toward the front 301 of the head (i.e., toward the forehead). Each of the three optical sensors 200 in FIG. 3A may irradiate the head 110 with optical signals from the optical sources of the optical sensor. The optical signals may distribute within the subject, for example across a half-sphere shape or other distribution pattern. At least a percentage of the optical signals may follow an arc (or "banana" shape) (or other path, as the exact type of path is not limiting) before exiting the head 110 and being detected by one or more optical detectors of the optical sensor. For example, referring to the optical sensor 200 identified by bracket 302, an optical signal (e.g., a light ray) 304a may be directed into the subject from an optical source 202 along the path shown in the direction of the arrows. Upon exiting the head 110, the optical signal 304a may be detected by one or more optical detectors 204 of the optical sensor 200. Similar behavior may be used to generate and detect optical signals 304b and 304c. Information about the subject may be determined from the detected optical signal, for example by analyzing the amplitude, phase, and/or frequency of the optical signal upon detection and by comparing such values to the amplitude, phase, and/or frequency of the optical signal when produced by the optical source. In some embodiments, the detected intensity alone is sufficient, and in some embodiments the detected intensity combined with information about the signal frequency is sufficient. Any suitable signal processing may be performed related to amplitude, phase, or frequency of the optical signal 304a (or other optical signals) to determine a quantity of interest.

As described already, any suitable number and configuration of optical sensors may be used. The use of three optical sensors as shown in FIG. 3A may facilitate analysis of multiple regions of a subject's brain (or, more generally, multiple regions or portions of a subject), such as both hemispheres of a subject's brain. However, one, two, three, four, five, or more optical sensors may be used to monitor one or more properties of interest of a subject's brain, and aspects of the present application apply equally well to one optical sensor of the type illustrated as to configurations having multiple such optical sensors. Also, the optical sensors may be arranged in manners other than that shown in FIG. 3A.

The absorbance of a material depends on the path length of optical signals through the material, and the concentration and the type of attenuating species in the material. The relative intensity of the optical signals detected by an optical detector and emitted by an optical sensor may provide an indication of the absorption properties of the region of tissue the optical signals pass through between the optical source and optical detector. The relative intensity between the emitted optical signals and the detected optical signals may be used to estimate an absorption coefficient, which may provide an indication of an extinction coefficient value and/or an estimated concentration of a quantity of interest in the subject. The Beer-Lambert Law provides a relationship between relative intensity and absorption properties, and may have the following formula:

$$-\log(I/I_0) = \mu_a L + G$$

In the Beer-Lambert Law, the relative intensity of the optical signals emitted by an optical source ($I_0$) to the optical signals detected by an optical detector (I) relates to the average path length traveled by photons from the optical source to the optical detector (L) and the absorption coefficient ($\mu_a$) of the material. The absorption coefficient depends on the molar extinction coefficient and the concentration of one or more species present in the material. In this manner, a concentration value of one or more species in the material can be estimated from measured intensity values based on known properties of the material, including the types of species present in the material and known molar extinction coefficients for those species. This process of determining a concentration from collected data, including measured intensity values, may be referred to as the inverse problem. In the equation above, an error term (G) can be introduced in estimating an absorption coefficient. The error term may account for the heterogeneity of the region of interest, such as different species contributing to the optical signals and/or scattering of the optical signals.

Precision of the estimation of the absorption properties of a material, and thus, the concentration of one or more species, may be improved by detecting optical signals emitted by the same optical source using two or more optical detectors. Because the depths to which the detected optical signals travel within the subject may depend at least in part on the distance between the optical source and the optical detector, using multiple optical detectors located at different distances from the optical source may provide information about different depths within the subject, and thus allow for comparison of such information. Accordingly, aspects of the application may process optical signals by comparing (or otherwise using) detected quantities representing an optical signal from a single optical source that is detected by multiple optical detectors located at different distances from the optical source. Such techniques, which are referred to in some embodiments herein as spatial differential techniques, may lead to a more precise estimate of the absorption properties of a subject's brain than from detecting optical signals using one optical detector alone.

Figure 3B:
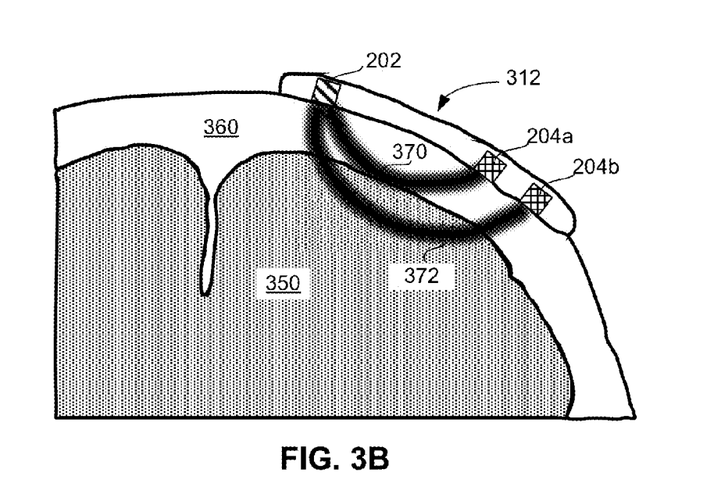
FIGS. 3B and 3C illustrate a schematic of optical paths through a subject's head.

FIG. 3B illustrates a cross-sectional view of a subject's head with a sensor 312 positioned to provide optical signals through a region of the subject's head. The structures of the subject's head can be approximated as having regions 350 and 360. Region 350 represents the subject's brain, and region 360 represents the structures of the subject's head that surround the brain, including bone, sinus, skin, and hair. Estimates of the absorption properties of region 350 corresponding to the brain can be achieved by emitting optical signals 370 and 372 from the optical source 202 of sensor 312 and detecting the optical signals with optical detectors 204a and 204b of sensor 312. Optical source 202 and optical detector 204a are positioned such that optical signals 370 substantially pass through region 360 of the subject's head. Optical detector 204b is positioned relative to the optical source 202 such that optical signals 372 pass through both regions 360 and 350 of the subject's head.

Absorption properties within region 350 can be estimated based on the optical signals detected at optical detectors 204a and 204b, and may provide a more precise estimation than from optical signals from one optical detector alone. Optical signals 370 pass substantially through region 360 and may provide an estimate for the absorption properties of region 360, which can be used in processing optical signals 372 to determine an estimate for the absorption properties of region 350. Accordingly, aspects of the application include comparing intensity values from measurements obtained by optical detectors 204a and 204b to improve the precision in determining an absorption property of a subject's brain. Such a technique may also reduce the effects of scattering in estimating absorption properties since optical signals 370 may provide a suitable estimate for scattering. The relative positions of the optical source 202 and the optical detector 204a may be arranged such that the optical signals emitted by the optical source 202 and the optical detector 204a pass primarily through region 370 of a subject's head.

In some embodiments, a modified Beer-Lambert Law may be used to determine a value for an absorption coefficient, which may be used to estimate the concentration of one or more species within a subject's brain. Such a modified Beer-Lambert Law may have the following equation:

$$-\log\left(\frac{I_2}{I_1}\right) = \mu_a(L_2 - L_1)$$

In the modified version of the Beer-Lambert Law, the relative intensity of the optical signals detected by a first optical detector ($I_1$) and optical signals detected by a second optical detector ($I_2$) relates to the difference of path lengths ($L_2 - L_1$) between the two optical signals and an absorption coefficient ($\mu_a$). Here, the first optical detector, such as optical detector 204a, is positioned closer to the optical source than the second optical detector, such as optical detector 204b. The path length from the optical source to the first detector ($L_1$) is shorter than the path length from the optical source to the second detector ($L_2$). In this equation, the absorption coefficient ($\mu_a$) may act as an estimate for the absorption coefficient of the material in a region corresponding to the difference between the two optical path lengths, such as within region 350 shown in FIG. 3B.

Applicant has appreciated that when using an optical sensor having multiple optical sources and multiple optical detectors, the determination of biological properties of interest may be improved by comparing optical intensities received by a number of optical detectors at different distances from a given optical source, and not necessarily all linearly arranged with respect to the optical source. Moreover, Applicant has appreciated that when a given optical source has associated with it first nearest neighbor detectors, second nearest neighbor detectors, and possibly higher order nearest neighbor detectors, comparing measured optical intensities at certain subsets of the neighboring detectors is beneficial compared to using certain other neighboring detectors. Examples are described further below in connection with FIGS. 5A and 5B. These techniques can be extended to multiple optical sources and optical detectors in a sensor to estimate absorption properties for discrete regions within a subject.

Figure 3C:
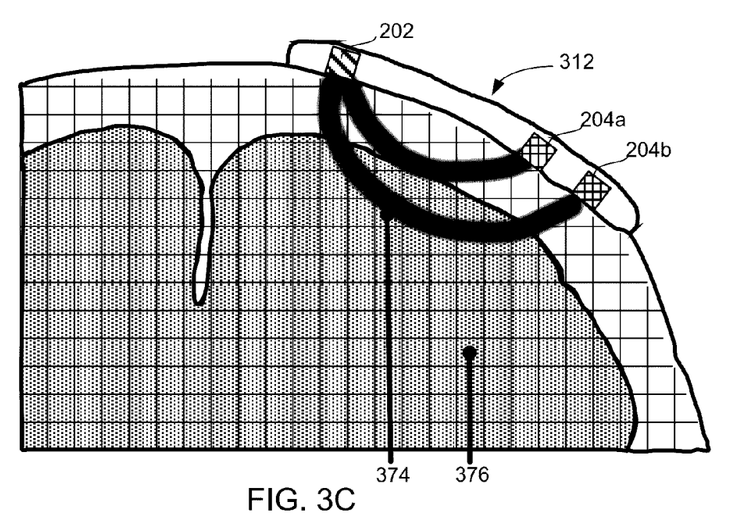

For context, the discrete regions within a subject (e.g., a subject's brain) may be considered voxels and defined by a three-dimensional location within the subject. FIG. 3C illustrates discretized regions as voxels, such as voxels 374 and 376, for the cross-sectional view of a subject's head shown in FIG. 3B. Estimates for tissue properties (e.g., absorption, chromophore concentration) can be resolvable for individual voxels by optical signals that pass through those voxels. For example, optical signals emitted by optical source 202 and detected by optical detector 204b may be used to resolve voxel 374, and in some instances, voxel 376. The resolution of voxels may depend on the number of optical signals from different optical source and optical detector pairs used to determine the optical properties. Aspects of the present application may facilitate analysis of a large number of voxels, such as between 20,000 and 40,000 voxels. The level of resolution for an optical property may vary among individual voxels since some voxels may have more optical signals that pass through than other voxels. In some embodiments, techniques of the present application may resolve voxels at a certain distance from a surface of the subject's head (e.g., in the range of 2 cm to 3 cm) with a desired level of resolution.

The relationship between measured optical signals and estimated optical properties can be expressed by the following equation:

$$y = Ax$$

In this equation, y is a vector of length N with elements corresponding to measurements for specific source-detector pairs, x is a vector of length V with elements corresponding to the optical properties for different voxels, and A is a N×V matrix, referred to as an A-matrix, with elements relating to the sensitivity of measurements of optical signals to changes in optical properties. Here, N and V are both positive integers. Values in the A-matrix may be determined from known relationships of how the optical properties of different species provide changes in optical signals. Any suitable number of elements may be included in either y, x, or the A-matrix. The vector y may include comparisons of measured optical intensities with a reference (e.g., model, another wavelength, a measurement at a different point in time). The optical properties for the individual voxels may be estimated based on the relation y=Ax.

A simplified example in which there are three measured signals (N=3) and four voxels (V=4) is shown in the following equation:

$$\begin{bmatrix} y_1 \\ y_2 \\ y_3 \end{bmatrix} = \begin{bmatrix} A_{1,1} & A_{1,2} & A_{1,3} & A_{1,4} \\ A_{2,1} & A_{2,2} & A_{2,3} & A_{2,4} \\ A_{3,1} & A_{3,2} & A_{3,3} & A_{3,4} \end{bmatrix} \begin{bmatrix} x_1 \\ x_2 \\ x_3 \\ x_4 \end{bmatrix}$$

Here, elements in the A-matrix relate perturbations in optical signals in the y-vector of measured optical signals to values in a voxels in the x-vector. Values in the A-matrix may also account for variability in the output power of different optical sources and/or sensitivity of different optical detectors in an array. These values may be determined by evaluating the optical sources and/or optical detectors and accounting for any variation by adjusting the values in the A-matrix. A user may input information about the variability in optical sources and/or detectors as part of processing the detected optical signals.

Precision in estimating optical properties of the voxels may be improved by combining measurements from multiple optical detectors. The combination of optical signals from optical detectors at different distances from an optical source may improve the precision in estimating an optical property of one or more voxels. Any suitable property of the optical signals may be combined, such as intensity. In some embodiments, a difference in optical intensity between two optical detectors may be used in determining optical properties of a subject. In some embodiments, a ratio of the optical intensity between two optical detectors may be used in determining optical properties of a subject.

In a sensor having multiple optical detectors, such as sensor 200 shown in FIG. 2A, there are multiple possible combinations of optical detectors which may be used for measurement comparison purposes. Applicant has appreciated that some combinations are more effective than others at improving the precision of an estimated optical property. As a result, performing processing for every optical source-optical detector pair may reduce the processing efficiency of the optical signals without providing benefits in precision of the quantified optical property for the voxels. Accordingly, aspects of the application include selecting combinations of measurements from different detectors for processing to quantify an optical property within a subject. Some embodiments include combining measurements from optical detectors that are different types of nearest neighbors (e.g., first nearest neighbor, second nearest neighbor, etc.) to an optical source. Data from measurements of optical detectors that are closest to one another, but neighbor the optical source in a different manner (e.g., as first nearest neighbor, second nearest neighbor, etc.) may be combined. In some embodiments, combinations of measurements for an optical source may include measurements from an optical detector that is a first nearest neighbor to the optical source and a second nearest neighbor to the optical source that has the smallest distance to the first optical detector. It should be appreciated that techniques for combining a first nearest neighbor optical detector and a second nearest neighbor optical detector may be used for a variety of arrangements of optical sources and detectors in a sensor and is not limited to the grid configuration shown in FIG. 2A.

Figure 4:
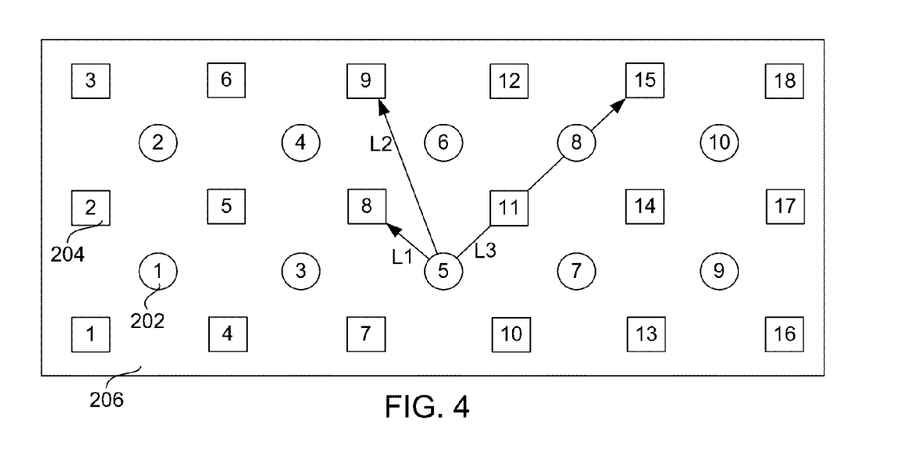
FIG. 4 illustrates in schematic form the layout of the optical sources and optical detectors of the optical sensor of FIGS. 2A and 2B, according to a non-limiting embodiment.

Optical signals from two or more optical detectors selected for a combination may be identified based on how the two optical detectors neighbor a common optical source. In a sensor, optical sources and optical detectors may be arranged such that an optical source has optical detectors that are first nearest neighbors, second nearest neighbors, third nearest neighbors, etc. FIG. 4 illustrates in schematic form the layout of the optical sources 202 and optical detectors 204 of the sensor 200. There are ten total optical sources 202 (represented by circles in FIG. 4 and numbered 1-10 for ease of explanation) and eighteen total optical detectors 204 (represented by squares in FIG. 4 and numbered 1-18 for ease of explanation) in the non-limiting embodiment of optical sensor 200, but it should be appreciated that other numbers of optical sources and/or optical detectors may be used, such that the various aspects of the present application are not limited to using any particular number of optical sources and optical detectors in an optical sensor. The number of optical sources and/or optical detectors may be selected in dependence upon a desired application of the optical sensor, keeping in mind data processing goals/constraints (e.g., a larger number of optical detectors will lead to a greater amount of data to process), and the desired size of the region of the head (or other subject) to study, among other potential considerations. For example, the number of optical sources and optical detectors may affect the size of the region when the spacing between optical sources and detectors is held constant.

As described previously, and as illustrated in FIG. 4, embodiments of the present application provide for a sensor for which more than one optical detector 204 detects optical signals produced by a particular optical source 202. For example, referring to FIG. 4, optical detectors 8, 9, and 15 may all detect optical signals produced by optical source 5 (as may other optical detectors). Optical detectors 8, 9, and 15 are located at increasing distances L1, L2, and L3, respectively, from the optical source 5, and may be considered as first nearest neighbor to optical source 5, second nearest neighbor to optical source 5, and third nearest neighbor to optical source 5, respectively. Higher order nearest neighbors (e.g., fourth nearest neighbor, fifth nearest neighbor, etc.) may also detect optical signals in some embodiments, depending on factors such as the strength of the optical signals produced by the optical sources, the distances between the optical sources and optical detectors, and the material into which the optical signals are being sent (e.g., tissue). Also, it should be appreciated that there are multiple detectors of a given nearest neighbor type for the optical source 5. That is, optical detectors 7, 8, 10, and 11 are all first nearest neighbors of the optical source 5. Optical detectors 5, 9, 12, and 14 are second nearest neighbors of the optical source 5. Optical detectors 6 and 15 are third nearest neighbors to the optical source 5.

Combinations of optical signals from multiple optical detectors can be selected based on the proximity of the optical detectors to each other and to an optical source. The multiple optical detectors may have different distances from the optical source such that the optical detectors are selected based on how they neighbor the optical source. Optical signals detected by the multiple optical detectors may have different path lengths through the subject. A first set of neighbors to the optical source may be at a first distance, a second set of neighbors may be at a second distance to the optical source, and a third set of neighbors may be at a third distance to the optical source. Additional sets of neighbors to the source may be included selecting combinations depending on the configuration and arrangement of optical sources and optical detectors in the sensor.

Combinations of optical detectors across different sets of neighbors to an optical source may be selected based on proximity of the optical detectors to each other. Optical detectors may be selected such that they have the smallest distance among the different sets of neighbors. Positions of the optical sources and optical detectors in the sensor may be stored in a memory of a computing device, such as host module 106 and/or central unit 108. The positions may be accessed during processing of the detected optical signals to provide an indication of which combinations of optical signals to process.

Figure 5A:
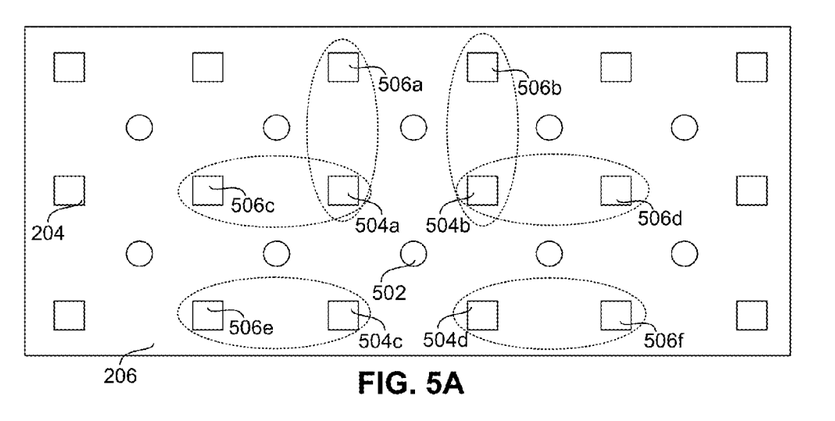
FIGS. 5A and 5B illustrate in schematic form pairs of optical detectors, the outputs of which may be combined to determine optical properties of a subject, according to a non-limiting embodiment.

In some embodiments, the signals from a first nearest neighbor optical detector and a second nearest neighbor optical detector may be combined if those optical detectors have the smallest distance from among the different combinations of first and second nearest neighbor detectors. An example is described with respect to FIG. 5A, which illustrates in schematic form the layout of a sensor showing combinations (in dotted ellipses) of first nearest neighbors and second nearest neighbors to the optical source 502 that have the smallest distances from among the different combinations of first and second nearest neighbors. As shown in FIG. 5A, the combination of optical source 502, a first nearest neighbor optical detector 504, and a second nearest neighbor optical detector 506 closest to the first nearest neighbor optical detector has a non-linear arrangement. That is, the components are not disposed with respect to each other along a same straight line. Exemplary pairs of closest first and second nearest neighbor optical detectors that neighbor optical source 502 shown in FIG. 5A include 504a and 506a, 504a and 506c, 504b and 506b, 504b and 506d, 504c and 506e, and 504d and 506f. It should be appreciated that not every combination of first nearest neighbor and second nearest neighbor of optical source 502 is illustrated as being of interest (reflected by the dotted ellipses). For instance, 506b is a second nearest neighbor optical detector, but because it is not spaced from the first nearest neighbor optical detector 504a by as short a distance as are second nearest neighbor optical detectors 506a and 506c, the benefits of combining signals from optical detector 504a and optical detector 506b may be less than that of combining signals from optical detectors 504a and 506b and less than combining signals from optical detectors 504a and 506c. Combining detector pairs that have the shortest spacing may provide improved estimates of optical properties of a subject's brain because a first detector of the pair that is closest to the optical source may act as an estimate for scattering and/or absorption from tissue and bone layers surrounding the subject's brain for the second detector of the pair. This estimate may be more precise than another detector of the same neighbor type to the source as the first detector because of the proximity between the first detector and the second detector.

Figure 5B:
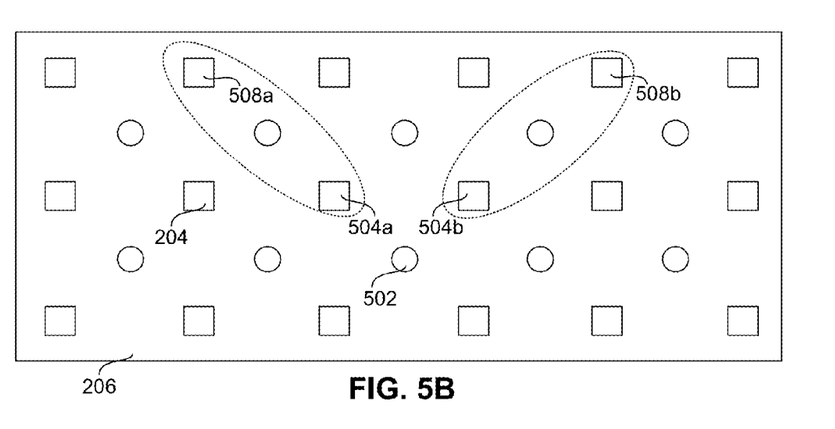

Combinations among different sets of nearest neighbors may extend beyond second nearest neighbors combined with first nearest neighbors. FIG. 5B illustrates in schematic form the layout of a sensor showing combinations (in dotted ellipses) of first nearest neighbors and third nearest neighbors to the optical source 502 that have the smallest distances from among the different combinations of first and third nearest neighbors. In the configuration of the sensor shown in FIG. 5B, the arrangement of optical source 502, first nearest neighbor 504a, and third nearest neighbor 508a closest to the first nearest neighbor 504a is linear. Likewise, the arrangement of optical source 502, first nearest neighbor 504b, and third nearest neighbor 508b closest to the first nearest neighbor 504b is linear. Exemplary pairs of closest first and third nearest neighbor optical detectors that neighbor optical source 502 shown in FIG. 5B include 504a and 508a, and 504b and 508b. Additionally or alternatively, combinations of closest third nearest neighbors to second nearest neighbors may be used in processing optical signals. In some embodiments, fourth and/or fifth nearest neighbors may also be combined with a different set of nearest neighbors.

Optical signals emitted by a source and detected by two optical detectors from different sets of nearest neighbors that have the smallest distance to each other may be combined in any suitable manner. Combinations of the optical signals may be determined by taking a difference and/or determining a ratio of the detected optical signal intensities between the two detectors. The ratio or difference in the detected signal intensities may be used to determine optical properties for one or more voxels in the subject. In some embodiments, a ratio or a difference in optical intensities detected at the two detectors may be used to quantify a property in a volume of a subject.

An A-matrix used in these calculations may differ from the A-matrix used in conventional DOT. Applying techniques that include taking a difference between optical signals from two optical detectors that are from different sets of nearest neighbors to an optical source may include an A-matrix that has a different number of elements in the matrix than the A-matrix used in conventional DOT. The A-matrix provides a relationship between the difference between measured optical signals for the two optical detectors and optical properties for voxels. Elements of the A-matrix may be created from elements of a conventional A-matrix. In some embodiments, the elements in the A-matrix may include elements which represent a difference between elements in a conventional A-matrix. An example where there are four voxels and three measured optical signal intensities $y_1$, $y_2$, and $y_3$, corresponding to the first, second, and third nearest neighboring optical detectors, respectively, is shown in the following equation:

$$\begin{bmatrix} y_1 - y_2 \\ y_2 - y_3 \end{bmatrix} = \begin{bmatrix} A_{1,1} - A_{2,1} & A_{1,2} - A_{2,2} & A_{1,3} - A_{2,3} & A_{1,4} - A_{2,4} \\ A_{1,1} - A_{3,1} & A_{1,2} - A_{3,2} & A_{1,3} - A_{3,3} & A_{1,4} - A_{3,4} \end{bmatrix} \begin{bmatrix} x_1 \\ x_2 \\ x_3 \\ x_4 \end{bmatrix}$$

Here, the A-matrix is a 2×4 matrix where elements in the matrix correspond to differences in A-matrix values corresponding to conventional A-matrix values that relate perturbations in optical properties to measured optical signals. The example discussed above describes a simplified version. It should be appreciated that these techniques can be expanded to accommodate any suitable number of detectors, voxels, and elements in an A-matrix. In some embodiments, approximately 100 to approximately 800 optical signals may be measured by optical detectors in a sensor. In some embodiments, optical properties for approximately 20,000 to approximately 40,000 voxels within a region of a subject may be resolved based on the optical signals.

Some embodiments include determining optical properties of a subject based on optical signals having different wavelengths. In some such embodiments, one of the wavelengths may be used as a reference wavelength against which properties of other wavelengths are compared. As an example, an optical source in a sensor may be configured to emit multiple wavelengths of optical emissions. Using extinction coefficients at different wavelengths, which may be determined in any suitable manner, optical signals at the multiple wavelengths may be used to determine estimates for absolute values of optical properties of a subject. Absolute values of concentrations of one or more species may be estimated from the values for the optical properties. The number of wavelengths may provide desired voxel resolution and/or desired optical properties and/or concentrations. Using data from multiple wavelengths may improve the accuracy of estimated absorption properties, and thus the concentration of one or more species in the subject, by reducing the effect of artifacts common to both the reference wavelength and another wavelength of the optical signals within the subject. Artifacts that contribute a type of noise independent of wavelength, such as a characteristic of the sensor array, variation in optical coupling of light from an optical source to the subject across optical sources in the array, subject's hair, and head curvature or geometry, can be accounted for using wavelength reference techniques because they have similar impacts on optical signals of different wavelengths. Using multiple wavelengths can reduce and/or eliminate the impact of these artifacts in determining optical properties of the subject because such artifacts may produce similar noise effects across different wavelengths and using a reference wavelength may allow cancelling out of such artifacts.

Different wavelengths of optical signals emitted by an optical source and detected by an optical detector may provide information to determine absolute values of biological properties of a region of a subject. One of the wavelengths may be used as a reference wavelength such that optical signals from the other wavelengths may be compared to the reference wavelength. The comparison between signals from one wavelength and the reference wavelength may provide an estimate for a difference in optical properties for the region, which may be used to determine an absolute value for a biological property for the region. In this manner, wavelength reference techniques may be used to determine biological properties for individual voxels.

For example, optical signals of a first wavelength detected by an optical detector and optical signals of a second wavelength detected by the optical detector may be used to determine an absolute value for a biological property (e.g., concentration of oxygenated hemoglobin, concentration of de-oxygenated hemoglobin). An absolute value for a biological property may be determined based on the difference and extinction coefficient information for the biological property. Additional wavelengths may be used to provide a more precise estimate for the biological properties where one of the wavelengths is used as a reference wavelength. In some embodiments, an optical source may be configured to emit at least five different wavelengths where one of the five wavelengths is used as a reference wavelength.

An example where there are five wavelengths ($\lambda_0$, $\lambda_1$, $\lambda_2$, $\lambda_3$, and $\lambda_4$) used to determine absolute values for concentration of oxygenated and de-oxygenated hemoglobin based on differences in absorption coefficients is shown in the following equation:

$$\begin{bmatrix} y_1 \\ y_2 \\ y_3 \\ y_4 \end{bmatrix} = \begin{bmatrix} A\delta\varepsilon_{HbO}^{\lambda_1-\lambda_0} & A\delta\varepsilon_{HbR}^{\lambda_1-\lambda_0} \\ A\delta\varepsilon_{HbO}^{\lambda_2-\lambda_0} & A\delta\varepsilon_{HbR}^{\lambda_2-\lambda_0} \\ A\delta\varepsilon_{HbO}^{\lambda_3-\lambda_0} & A\delta\varepsilon_{HbR}^{\lambda_3-\lambda_0} \\ A\delta\varepsilon_{HbO}^{\lambda_4-\lambda_0} & A\delta\varepsilon_{HbR}^{\lambda_4-\lambda_0} \end{bmatrix} \begin{bmatrix} [HbO] \\ [HbR] \end{bmatrix}$$

Here, $y_1$, $y_2$, $y_3$, and $y_4$ correspond to the comparisons between each of the first ($\lambda_1$), second ($\lambda_2$), third ($\lambda_3$), and fourth ($\lambda_5$) wavelengths and the reference wavelength ($\lambda_0$), A corresponds to an element of the A-matrix for the pair of optical source and optical detector, and $\delta\varepsilon_{HbO}^{\lambda_1-\lambda_0}$, $\delta\varepsilon_{HbO}^{\lambda_2-\lambda_0}$, $\delta\varepsilon_{HbO}^{\lambda_3-\lambda_0}$, and $\delta\varepsilon_{HbO}^{\lambda_4-\lambda_0}$ correspond to differences in the extinction coefficient for oxygenated hemoglobin for the different wavelengths, $\delta\varepsilon_{HbR}^{\lambda_1-\lambda_0}$, $\delta\varepsilon_{HbR}^{\lambda_2-\lambda_0}$, $\delta\varepsilon_{HbR}^{\lambda_3-\lambda_0}$, and $\delta\varepsilon_{HbR}^{\lambda_4-\lambda_0}$ correspond to differences in extinction coefficient for de-oxygenated hemoglobin for the different wavelengths, and [HbO] and [HbR] are the concentrations of oxygenated and de-oxygenated hemoglobin, respectively, for the voxel.

Additionally or alternatively, techniques that measure optical signals at different wavelengths may be used in combination with selection of pairs of optical detectors from among different sets of nearest neighbors as previously described, for example in connection with FIGS. 5A and 5B. Pairs of optical detectors may provide estimates of optical properties at different wavelengths for a voxel, and those estimated optical properties may be used to determine an estimate for biological properties (e.g., HbO and HbR) for the voxel.

In some embodiments, optical source 502 may be configured to emit multiple wavelengths where one of those wavelengths can be used as a reference wavelength to determine estimates for biological properties (e.g., HbO and HbR) for individual voxels. For example, optical signals from a first wavelength detected by 504a and 506c can be used to determine a signal for the first wavelength. Optical signals from a second wavelength, acting as a reference wavelength, detected by 504a and 506c can be used to determine a signal for the second wavelength. A difference between the signals for the first and second wavelengths may be used to estimate biological properties of one or more voxels, including concentration of oxygenated hemoglobin, concentration de-oxygenated hemoglobin, and/or oxygen saturation for a voxel.

When multiple wavelengths are used for comparison purposes, with one or more such wavelengths serving as a reference wavelength, any suitable number of wavelengths may be used. In some embodiments, at least three wavelengths are used, with one serving as a reference wavelength. Signals from two of the wavelengths are processed in combination with the reference wavelength. In some embodiments, five wavelengths may be used where one of the five wavelengths acts as the reference wavelength. Signals from four of the wavelengths may be processed in combination with the reference wavelength. An optical source may be configured to emit multiple wavelengths in a coincident manner. Optical components in the optical source may be arranged and configured to focus optical signals emitted by the optical source to one location.

Figure 6:
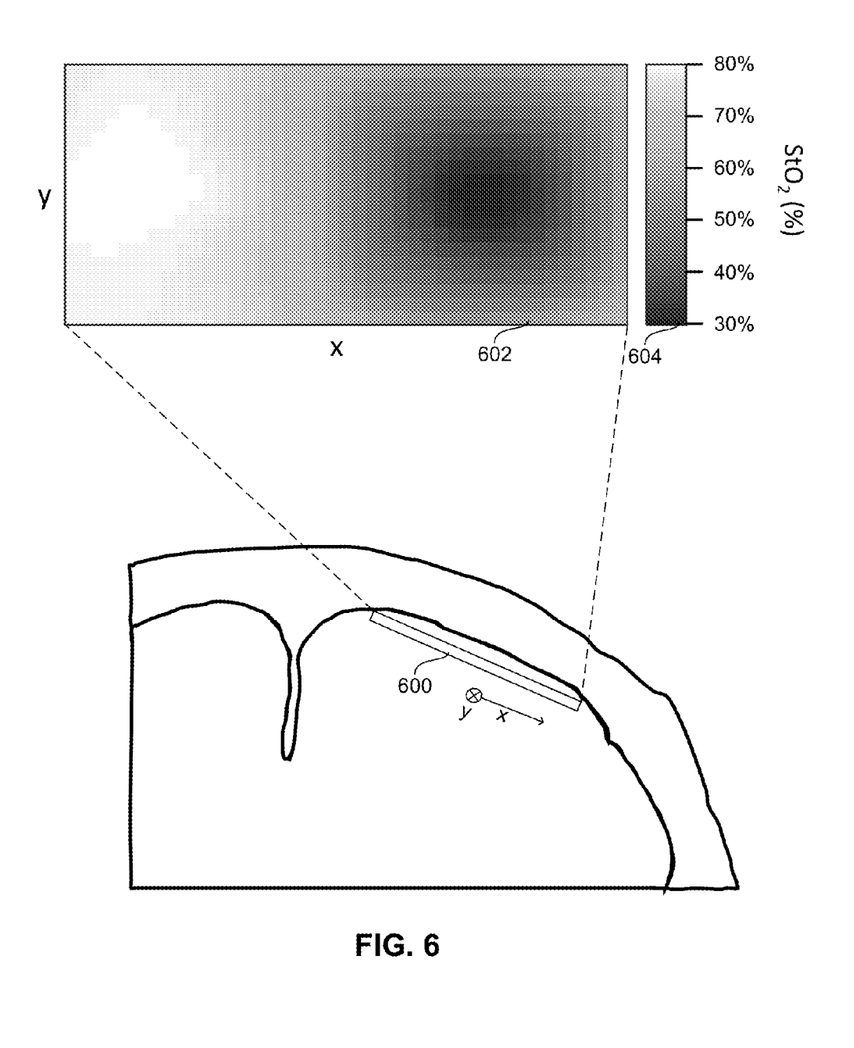
FIG. 6 shows an exemplary image of a cross-sectional view of a region of a subject's brain as may be generated according to a non-limiting embodiment.

Once the values of optical properties and/or biological properties (e.g., concentrations of species of interest (e.g., hemoglobin)) are determined, an image may be generated and displayed, such as on display 112. The values may correspond to different voxels such that an image provides a map of the optical properties within a subject. In this manner, the display may be configured to display a quantified value of an optical property and/or a biological property. The values displayed can be displayed in any suitable way to achieve a desired image. Values may be represented numerically and/or by color coding, such as through a heat map, in an image. An image may provide different cross-sectional views of the subject's head, such as by brain hemisphere. The values may represent averages across voxels, or averages across cross-sectional slices of the target object (e.g., the brain). In some embodiments, the data may be collected substantially in real time, for example at a rate of one frame per second, between 1 and 30 frames per second, 1 frame every few seconds, or any rate or range of rates within such ranges. In such instances, an image may be generated and/or refreshed at any such rate or a fraction of that rate. An image may illustrate indications of amount or concentration of species (e.g., oxygenated hemoglobin, de-oxygenated hemoglobin, oxygen saturation amount) estimated from optical signals that correspond to locations within the subject's brain, such as may be detected by a sensor according to aspects of the present application, such as the sensor shown in FIG. 2A. FIG. 6 shows an exemplary image 602 of a type which may be generated according to an aspect of the application, and specifically illustrates a view of a subject's brain within a plane perpendicular to region 600 shown in FIG. 6. Image 602 provides estimates of the tissue oxygen saturation of a slice proximate a top portion of the grey matter of the brain. Region 600 corresponds to the x-axis of image 602, and the y-axis of image 602 extends perpendicular to region 600. Image 602 is a grayscale converted color image where variation in shade provides an indication of the percentage of oxygen saturation (StO2) within the subject's brain. Darker shades indicate lower oxygen saturation percentages than lighter shades such that 30% oxygen saturation is represented by the color black and 80% saturation is represented by the color white. In exemplary image 602, the right portion of the image has a darker section in comparison to the left section of the image, providing an indication that the right portion of the slice perpendicular to region 600 has a lower oxygen saturation percentage than the left portion of the slice. It should be appreciated that other types of images may alternatively be generated. Colors, hues, numbers, shapes may be used to provide an indication of variation in the amount of species (e.g., oxygenated hemoglobin, de-oxygenated hemoglobin, oxygen saturation amount) within an image of a subject's brain.

The aspects of the present application may provide one or more benefits, some of which have been previously described. Now described are some non-limiting examples of such benefits. It should be appreciated that not all aspects and embodiments necessarily provide all of the benefits now described. Further, it should be appreciated that aspects of the present application may provide additional benefits to those now described.

Aspects of the present application provide techniques for combining measurements from at least two optical detectors based on how the at least two optical detectors neighbor an optical source. By determining a difference in intensity between optical signals measured by two of the optical detectors, processing of the optical signals may be simplified and provide more precise absolute values of optical and/or biological properties of regions of a subject, such as oxygenated hemoglobin, de-oxygenated hemoglobin, and oxygen saturation. The difference in optical signals may reduce contributions from scattering such that an absolute value of an optical property more accurately reflects a region of the subject.

Aspects of the presentation application provide the ability to determine absolute values for optical and/or biological properties for a significant number of voxels (e.g., greater than 10,000 voxels) representing different regions of a subject. By constructing the relationship between measured optical signals and optical and/or biological properties in a matrix format, processing optical signals for such a large number of voxels can be achieved. The large number of voxels may provide improved resolution in imaging the subject and allow improved detection for features and characteristics in the subject's brain. Additionally, the techniques described herein reduce the need to model parameters of a subject such that more of the processing is based on the measurements of the optical signals themselves.

Aspects of the present application may be used to measure absolute values of optical and/or biological properties of the subject's brain, rather than changes in properties. These techniques can reduce the need to characterize and calibrate the optical sources to emit the same optical power, providing flexibility in the overall design of the sensor array while achieving a desired level of precision of the absolute values. Additionally, such techniques can reduce contributions from the attenuation of optical signals by one or more layers surrounding the brain, such as skin, hair, scalp and bone. Selecting combinations of measurements from optical detectors such that a measurement from one of the optical detectors provide an estimate of the attenuation from these layers allows for absolute values of optical properties to be determined, which may reduce the processing costs of modelling the properties of these layers. By comparing optical signals at a detector for different wavelengths emitted by an optical source, absolute values for biological properties, such as concentration of oxygenated and de-oxygenated hemoglobin can be achieved.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

What is claimed is:

1. An apparatus comprising:
   a first optical source disposed at a first position and configured to emit a first optical signal of a first wavelength;
   an arrangement of optical detectors, at least some of which are positioned at different distances from the first optical source, including a first subset of multiple optical detectors positioned a first distance from the first optical source and a second subset of multiple optical detectors positioned a second distance greater than the first distance from the first optical source, wherein the first subset of multiple optical detectors and the second subset of multiple optical detectors are configured to receive the first optical signal,
   wherein a first optical detector of the first subset of multiple optical detectors is configured to produce a first output signal indicative of a first received optical intensity of the first optical signal,
   wherein a second optical detector of the second subset of optical detectors is configured to produce a second output signal indicative of a second received optical intensity of the first optical signal, and
   wherein a third distance between the first optical detector of the first subset of multiple optical detectors and the second optical detector of the second subset of multiple optical detectors is a smallest distance from among a plurality of distances between the first optical detector and the multiple optical detectors of the second subset; and
   a processor coupled to the first and second subsets of multiple optical detectors and configured to receive from the first and second subsets of multiple optical detectors signals detected by those detectors, including the first output signal from the first optical detector and the second output signal from the second optical detector, the processor being further configured to process in combination the first output signal and the second output signal.

2. The apparatus of claim 1, wherein the processor is configured to process in combination the first output signal and the second output signal by determining a difference between the first received optical intensity and the second received optical intensity.

3. The apparatus of claim 1, wherein the processor is coupled to a memory and configured to access from the memory information identifying the plurality of distances between optical detectors of the second subset and the first optical detector.

4. The apparatus of claim 1, wherein the first optical source, the first optical detector, and the second optical detector are not disposed on a same straight line.

5. The apparatus of claim 1, wherein the first optical source and the arrangement of optical detectors are disposed on a flexible substrate to form a flexible array, such that a distance between the first optical source and the first optical detector is dependent on a flexed state of the flexible substrate.

6. The apparatus of claim 1, wherein the first optical source is configured to emit a second optical signal at a second wavelength at a same location as the first wavelength, the first optical detector is configured to produce a third output signal indicative of a third received optical intensity of the second optical signal, and the second optical detector is configured to produce a fourth output signal indicative of a fourth received optical intensity of the second optical signal.

7. The apparatus of claim 6, wherein the processor is further configured to process in combination the first output signal, the second output signal, the third output signal, and the fourth output signal.

8. The apparatus of claim 1, wherein the processor is configured to determine from processing in combination the first output signal and the second output signal, a property of a subject through which the first optical signal passes.

9. The apparatus of claim 8, wherein the property is absolute oxygen saturation.

10. The apparatus of claim 8, wherein the property is absolute total hemoglobin.

11. The apparatus of claim 8, further comprising a display coupled to the processor and configured to display a quantified value of the property.

* * * * *